United States Patent [19]

Beausoleil et al.

[11] Patent Number: 5,450,948
[45] Date of Patent: Sep. 19, 1995

[54] CONTAINER AND PACKAGE FOR TRANSPORTING TEMPERATURE SENSITIVE SAMPLES

[75] Inventors: Jackie L. Beausoleil, New Ipswich; Joye A. Vautour, Greenville, both of N.H.; Augiras G. Manomaitis, Pepperell, Mass.; James C. Helzer, Wichita, Kans.; Michael P. Swett, Manchester, N.H.

[73] Assignee: GTEL Environmental Laboratories, Inc., Milford, N.H.

[21] Appl. No.: 227,644

[22] Filed: Apr. 14, 1994

[51] Int. Cl.⁶ .................... B65D 81/26; B65D 81/107
[52] U.S. Cl. ...................... 206/204; 53/428; 53/472; 206/522; 206/523
[58] Field of Search ............... 53/499, 472, 400, 428; 206/204, 522, 523, 587, 593, 594

[56] References Cited

U.S. PATENT DOCUMENTS

| | | |
|---|---|---|
| 916,729 | 3/1909 | Munyon . |
| 1,269,197 | 6/1918 | Mendenhall . |
| 2,969,891 | 1/1961 | Presnick .................... 220/73 |
| 3,181,693 | 5/1965 | Freistat ..................... 206/1 |
| 3,241,661 | 3/1966 | Zamzow et al. ............. 206/46 |
| 3,415,358 | 12/1968 | Faller ........................ 206/46 |
| 3,464,579 | 9/1969 | Asenbauer .................. 220/4 |
| 3,811,747 | 5/1974 | Levin ........................ 312/308 |
| 3,955,704 | 5/1976 | Smith et al. ................ 220/21 |
| 4,037,722 | 7/1977 | Bremer ...................... 206/523 |
| 4,106,597 | 8/1978 | Shook et al. ............... 190/42 |
| 4,150,464 | 4/1979 | Tracy ........................ 24/77 R |
| 4,171,555 | 10/1979 | Bakker et al. .............. 24/200 |
| 4,235,065 | 11/1980 | Freeman .................... 53/547 |
| 4,240,547 | 12/1980 | Taylor ....................... 206/204 |
| 4,640,418 | 2/1987 | Lowry ....................... 206/499 |
| 4,721,237 | 1/1988 | Leslie ....................... 224/148 |
| 4,826,003 | 5/1989 | Levy ......................... 206/523 |
| 4,836,374 | 6/1989 | Hutchins et al. ........... 206/373 |
| 4,884,684 | 12/1989 | Bernardin et al. .......... 206/523 |
| 4,949,840 | 8/1990 | Brown ....................... 206/523 |
| 4,955,480 | 9/1990 | Sexton ...................... 206/523 |
| 4,964,509 | 10/1990 | Insley et al. ............... 206/523 |
| 5,040,678 | 8/1991 | Lenmark, Sr. et al. ...... 206/443 |
| 5,080,225 | 1/1992 | Russo et al. ............... 206/204 |
| 5,105,970 | 4/1992 | Malone et al. ............. 206/523 |
| 5,131,543 | 7/1992 | Stephens ................... 206/523 |
| 5,236,088 | 8/1993 | Dhority et al. ............. 206/523 |

Primary Examiner—Jimmy G. Foster
Attorney, Agent, or Firm—Banner & Allegretti, Ltd.

[57] ABSTRACT

A package for transporting temperature sensitive samples, such as ground and water samples to be analyzed, includes a lightweight plastic insulated container (cooler) body and cover. A plurality of sample containers are snugly retained within respective internal cavities of one or more foamed plastic blocks. In turn, the foamed plastic blocks are packed inside of the cooler body with bubble-wrap used to fill the interstitial space within the cooler. A liquid absorbent layer is placed in the bottom of the cooler and a plastic liner bag encases the sample containers and plastic blocks. A strap and plastic snap-clip arrangement securely holds the cooler cover on the cooler body during transportation. The sample containers may readily be removed for filling in the field, then repacked with ice added to maintain the temperature of the samples within the required range.

10 Claims, 4 Drawing Sheets

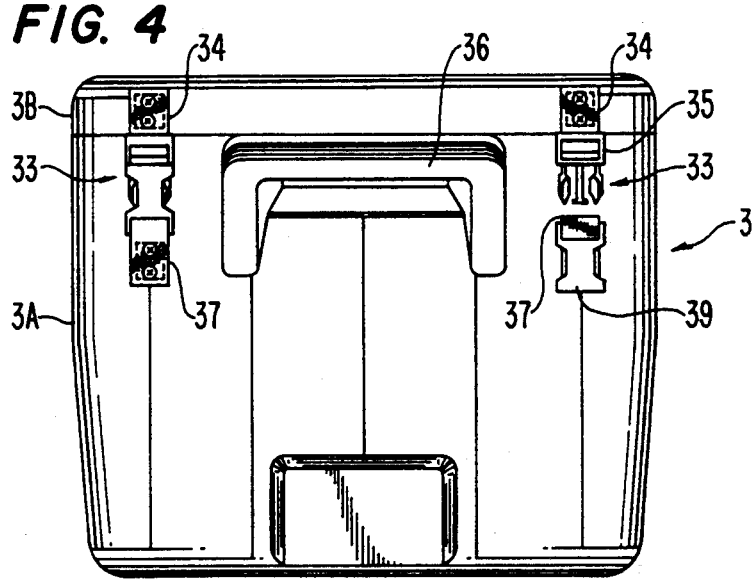
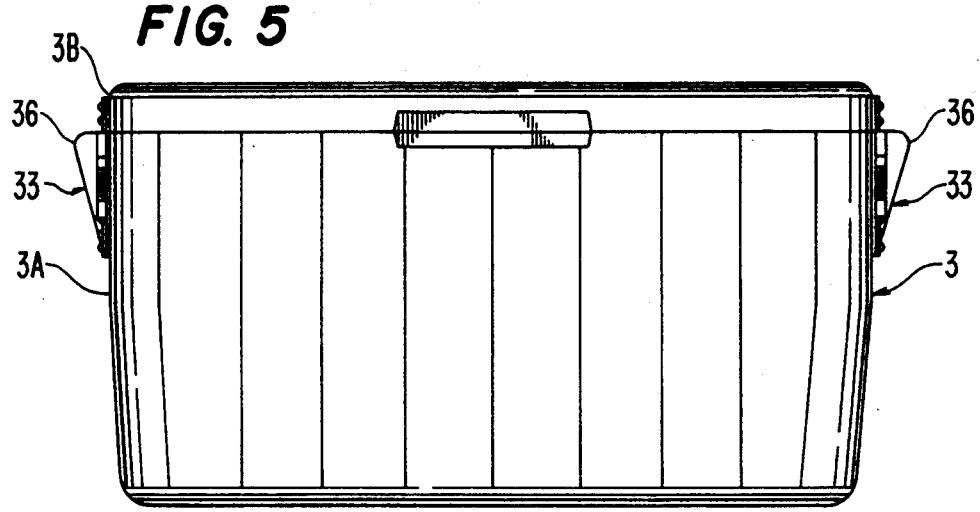
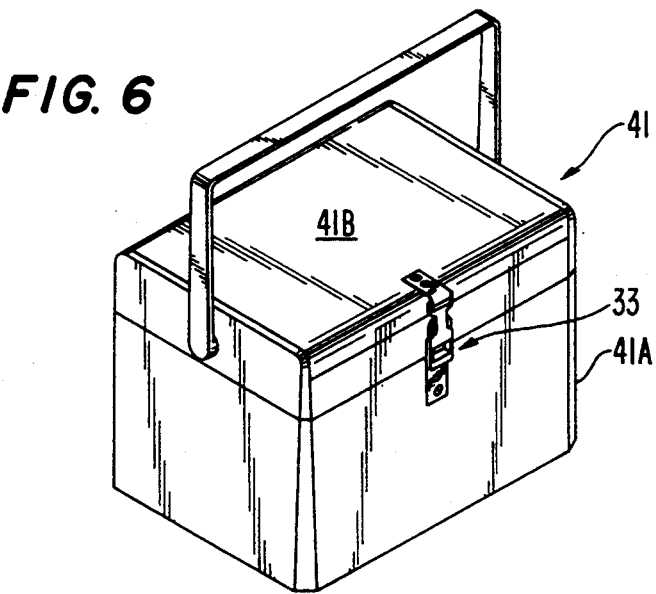

CONTAINER AND PACKAGE FOR TRANSPORTING TEMPERATURE SENSITIVE SAMPLES

BACKGROUND OF THE INVENTION

The present invention relates to shipping containers and packaging arrangements therefor. In particular, the invention pertains to insulated containers and packaging suitable for transporting temperature sensitive samples to be analyzed, such as soil and water samples.

With the widespread problems and concerns with environmental contamination caused by industry and business, a substantial demand has developed for analytical services that provide chemical analyses of soil and groundwater samples. Soil and water samples to be analyzed for contaminants must be transported, often over long distances by truck and air, from the field to the laboratory. Obviously, the sample containers must be packaged in such a manner as to provide adequate protection against breakage. To ensure reliable test results, it is also necessary that the samples be maintained within a certain temperature range during transportation to the lab. For the same reason, it is also important that the samples be packed so as to minimize exposure of the samples to contaminated environments while en route.

Conventionally, sealable sample containers of glass are randomly dispersed inside of a standard recreational-type cooler together with packing material such as styrofoam peanuts, bubble-wrap or paper. Since standard arrangements for retaining a cover over the cooler opening (e.g., latches, hinges or a friction-fit) are not designed nor able to withstand the rigors of conventional freight transportation, the usual technique is to tape the cooler cover shut with strapping tape or the like. Such a package is first shipped off to the customer by the analytical services company. The customer opens the cooler, removes and fills the sample containers with sample material, then repacks the sample containers in the cooler with ice for shipment back to the lab - often without additional packing material.

The conventional approach results in a messy package that is difficult to open and close. This imposes great inconvenience and inefficiency on both the customer who must open, unpack then repack the cooler, and the service company that must initially pack the cooler for shipment to the customer, then open and unpack it when it is returned. The strapping tape holding the cover on is difficult and time consuming to apply and remove. Once the container is opened, the sample containers must randomly be fished out of the packing material (and ice after the return trip). Moreover, breakage of the containers due to the inadequate use of packing material is common. In addition to the obvious waste that such breakage entails, a health hazard is presented due to the contaminants that may exist in the sample materials.

The unpacking procedure is particularly messy and inefficient on return of the samples to the analytical service company. The customer typically will have mixed ice with loose packing material. By the time the package reaches the lab, the ice will have melted, partially or completely, creating a soupy mess from which the sample containers must be retrieved. Additionally, any paper packaging material will have lost most of its effectiveness upon getting wet, potentially resulting in broken containers and leaked material which may be hazardous.

Various approaches have been taken in the design of specialized shipping containers intended to better accommodate bottles or other fragile containers, and/or to provide thermal insulation to the contents.

Failer U.S. Pat. No. 3,415,358 and Zamzow et al. U.S. Pat. No. 3,241,661 each disclose specialized bottle packages for the shipment of bottles of liquid. The Failer package utilizes a paperboard carton with an inner layer designed to absorb and contain liquid in the event one of the bottles breaks in transit. Zamzow et al. disclose an impact resistant package comprising a body of plastic foam material for holding the bottles and a pair of end covering members held on the body with straps.

Leninark, Sr. et al. U.S. Pat. No. 5,040,678 discloses an insulated biological transport container comprising a zippered cloth jacket surrounding a plastic encasement portion and sliding cover. A shock absorbing block having holes to retain vials of sample material fits into the encasement portion. Cooling packets are positioned in the shock absorbing block and optionally in a cooling chest surrounding the jacket.

Mendenhall U.S. Pat. No. 1,269,197 discloses a heavy-duty insulated shipping container having a removable lid securely retained on the container body by fasteners comprising two threadably engageable shanks, each having a loop at one end. The loop of one shank is hingedly connected by a strap to the container body. The loop of the other shank is engageable with a corresponding protruding lug on the lid. By threading one shank onto the other, the fastening devices are adapted to draw the lugs downwardly to bind the lid to the container body.

None of the packaging arrangements disclosed in the above-mentioned patents are particularly suited for the freight transportation of fragile sample containers that must be returned together with ice. Additionally, none of the patents teaches an arrangement that is readily and inexpensively adaptable from existing low-cost, lightweight and highly durable containers such as recreational-type coolers.

SUMMARY OF THE INVENTION

In view of the above, it is a primary object of the present invention to provide a transportation container and packaging arrangement that is particularly suited for the shipping of temperature sensitive soil and water samples, using ordinary shipping channels.

In particular, it is an object of the invention to provide an insulated sample container that affords the contents adequate protection and which is easily handled, opened, and closed.

A further object of the invention is to provide a packaging arrangement and method that simplifies and facilitates the procedure for (1) adequately packing empty containers for shipment to a customer; (2) unpacking, then adequately repacking, the sample containers with ice by the customer in the field or at its facility; and (3) unpacking and sorting at the lab filled sample containers returned by the customer.

It is yet another object of the invention to provide an insulated sample container that is readily and inexpensively adapted from existing low-cost, lightweight and highly durable recreational-type coolers.

Still another object of the invention is to provide an inexpensive transportation package that satisfies governmental standards, e.g., U.S. Department of Transportation (DOT) and United Nations standards, for the transportation of hazardous materials.

These and other objects are achieved by the present invention which, in one aspect, is embodied in a package for transporting temperature sensitive soil and water samples. The package includes a relatively rigid outer container having heat insulative walls defining an interior space, and a plurality of packing elements contained within and substantially filling the interior space. The packing elements include a sealable sample container and a foamed plastic block having an internal cavity. The sample container is snugly retained within the internal cavity of the block. The packing elements also include plastic bubble-wrap at least partially surrounding the sample container and block, and substantially filling the interstitial interior space of the outer container.

In a second aspect, the invention is embodied in a relatively rigid heat insulated transportation container. The container comprises a container body having relatively rigid heat insulative wall panels forming container sides and a container bottom. The container body defines an interior space and a container opening. A relatively rigid heat insulative container cover is fittable over the container opening to substantially seal the same, and is movable to open and close the container. A strap and clip assembly is provided for removably securing the container cover over the container opening. The strap and clip assembly includes a first relatively flexible strap having a first clip member attached at one end thereof, and an opposite end attached to one of the container body and container cover. The first clip member comprises a resilient locking element. A second relatively flexible strap has a second clip member attached at one end thereof, and an opposite end attached to one of the container body and container cover. The second clip member comprises a locking slot for receiving the resilient locking element of the first clip member in such a manner that the first clip member is snappingly engageable with the second clip member.

In a third aspect, the invention is embodied in a method of packing a cooler for transporting temperature sensitive soil and water samples. An absorbent pad is placed inside and along a bottom surface of the cooler. At least one layer of bubble-wrap is placed inside of the cooler on top of the absorbent pad. An open plastic liner bag is placed inside the cooler on top of the bubble-wrap. A sealable sample container is placed into a cavity of a foamed plastic block to form a block/container unit. The block/container unit is placed within the plastic liner bag. Bubble-wrap is placed within the liner bag and around the block/container unit so as to prevent movement of the sample container within the outer container. The plastic liner bag is closed off, and the cooler is closed with a cooler cover.

In a fourth aspect, the invention is embodied in a method of packing temperature sensitive sample material for transportation. The sample material is sealed in a sample container. The sealed sample container is placed into a recess of a corresponding foamed plastic block to form a block/container unit. The block/container unit is packed with bubble-wrap inside of a cooler, leaving a top side of the block/container unit exposed. The exposed top side of the block/container unit is covered with ice, and an additional layer of bubble-wrap is placed on top of the ice. Finally, the cooler is closed with a cooler cover.

The above and other objects, advantages and features of the invention will be readily apparent and fully understood from the following detailed description of the preferred embodiments, taken in connection with the appended drawings.

BRIEF DESCRIPTION OF THE DRAWINGS

FIG. 4 is an end elevational view of the transportation container shown in FIG. 1.

FIG. 5 is a side elevational view of the transportation container shown in FIG. 1.

FIG. 6 is a perspective view of a second smaller transportation container in accordance with the invention.

DETAILED DESCRIPTION OF THE PREFERRED EMBODIMENTS

Figure 1:
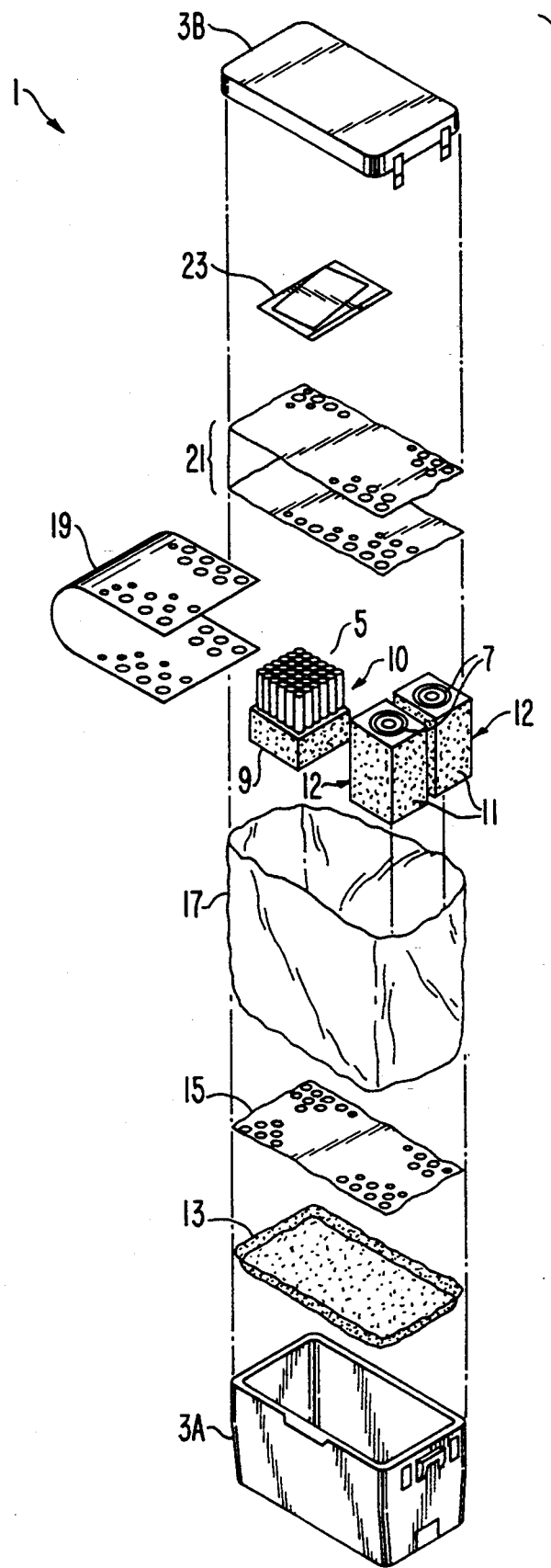
FIG. 1 is an overall exploded perspective view of a first transportation container and package in accordance with the present invention.
Figure 2:
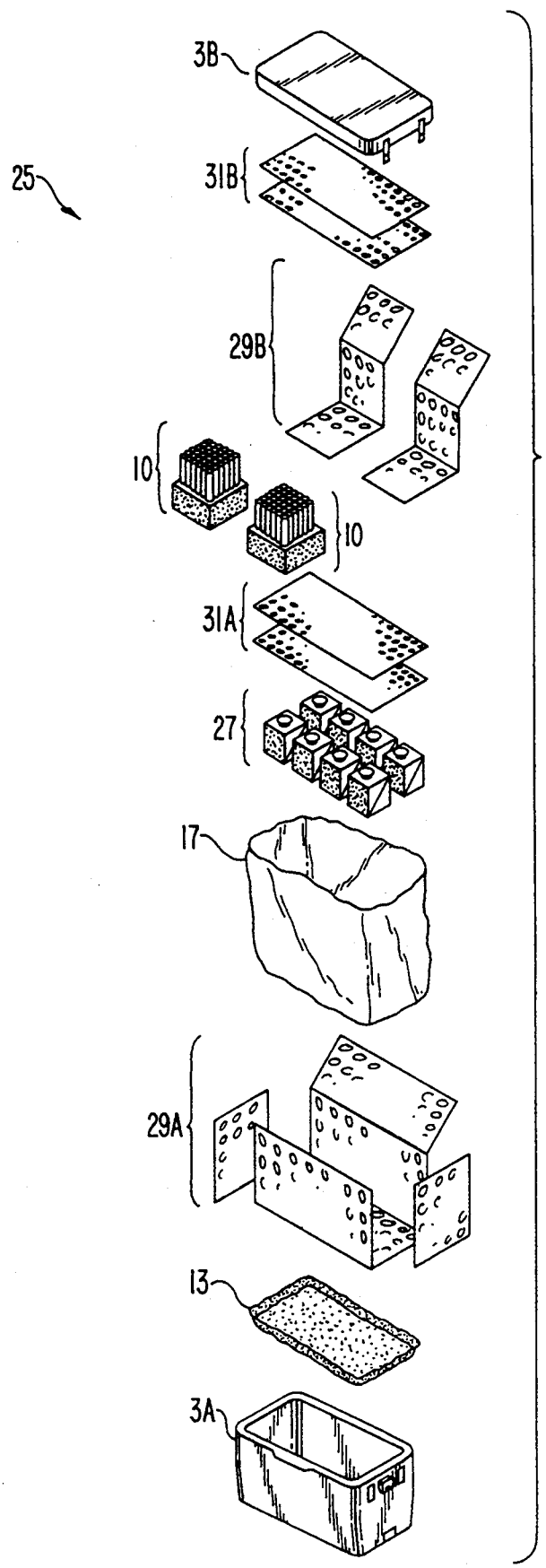
FIG. 2 is an overall exploded perspective view of a second transportation container and package in accordance with the invention.
Figure 3:
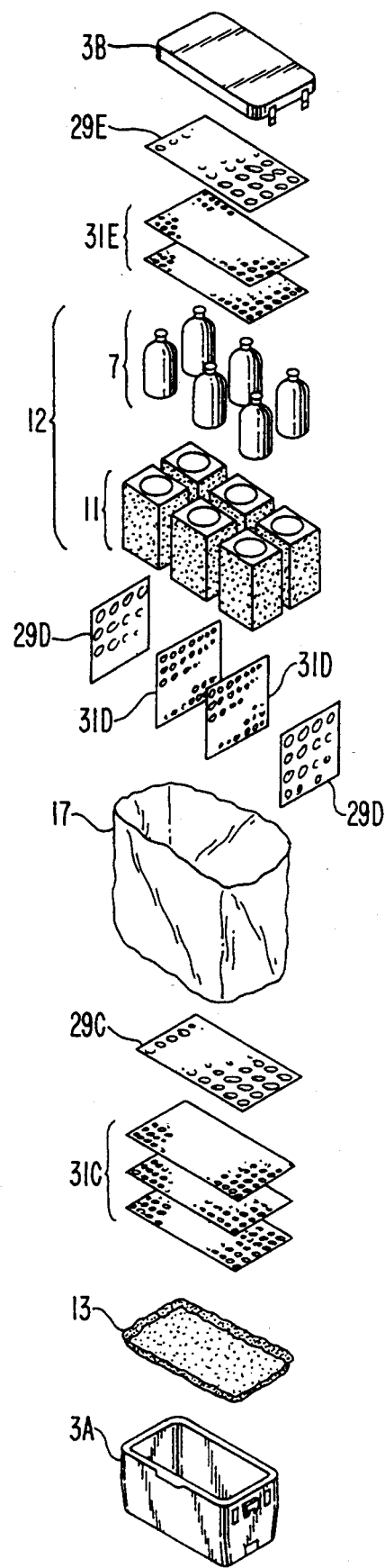
FIG. 3 is an overall exploded perspective view of a third transportation container and package in accordance with the invention

FIGS. 1-3 illustrate alternative packaging arrangements for the shipment of fragile sample containers in accordance with the present invention. Each is covered by a certification issued by the U.S. Department of Transportation (on behalf of the U.S. and the United Nations) for the transportation of hazardous materials.

Although the packaging arrangements are specifically intended for the transportation of temperature sensitive soil and water samples, it will be understood that the advantages of the invention may be realized in the transportation of various other materials, both hazardous and non-hazardous.

The illustrated packaging arrangements find application in both the shipment of empty sample containers to the customer, and for the return by the customer of filled sample containers to the lab. As will be described, the arrangements are particularly suitable for the packaging of temperature sensitive sample containers that are to be filled with sample material and repacked by the customer with ice.

Referring first to FIG. 1, transportation package 1 comprises a 48 quart capacity insulated outer container (cooler) 3 including a cooler body 3A and a removable cover 3B. The cooler shown is a modified Coleman Polylite48 (Coleman No. 5286B), wherein both the cooler body 3A and cover 3B comprise high density polyethylene shells defining heat insulative panels. The assembled cooler 3 is illustrated in FIGS. 4 and 5 and will be described in greater detail hereinafter.

Packed within cooler 3 are sealable sample containers made of vapor and liquid impervious material such as glass. In the illustrated embodiment of FIG. 1, package 1 contains 25 40 mL glass vials 5 and two one liter glass bottles 7. Each is sealed with a plastic, e.g., polypropylene, screw-on cap. Vials 5 are snugly retained in corresponding through-cavities of a single foamed plastic, e.g., polyurethane, block 9 measuring $7\frac{3}{4}'' \times 7\frac{3}{4}'' \times 3\frac{3}{4}''$ to form a block/container unit 10. The one liter bottles 7 are similarly snugly retained within the respective through-cavities of two foamed plastic blocks 11, each measuring $5\frac{3}{8}'' \times 5\frac{3}{8}'' \times 8\frac{1}{2}''$, to form two block/container units 12.

Blocks 9 and 11 provide shock-absorbing protection to the sample containers 5 and 7 and also serve to maintain the containers in an orderly arrangement. Open tops and bottoms of the container receiving cavities of blocks 9 and 11 facilitate the cooling of the containers 5 by ice placed thereabove and below, as will be described.

Suitable foam blocks 9,11 and sample containers 5,7 are available, e.g., from Eagle Picher, Inc. and I-CHEM, Inc. Obviously, foam blocks and sample containers of different sizes and configurations may be utilized as the particular need dictates. Likewise, different types and sizes of coolers may be employed. For example, for fewer or smaller sample containers, Coleman Polylite coolers are available in 24 and 32 quart sizes. A 10 quart cooler that may be used in the invention is the Coleman FlipLid10. Before use, these coolers should be modified in accordance with the teachings herein.

The block/container units 10 and 12 are packed inside of cooler body 3A, for shipment to the customer, in the following manner.

First, a liquid absorbent pad 13 is positioned along the inner bottom surface of the cooler to absorb the leaked contents of any of the sample containers that may escape into the bottom of the cooler. Such pads are sold, e.g., by 3M Company as "Universal Sorbent Pads" (Lab Safety and Supply No. QB-20020). Enough absorbent material should be placed in the bottom of the cooler to absorb the contents of the largest sample container.

Next, one or two layers of plastic bubble-wrap 15 (only one layer is illustrated in FIG. 1) is placed on top of absorbent pad 13. A suitable bubble-wrap product is available from BrownCor, Inc. under product Nos. B4-1502 (13/16" bubble diameter) and B4-1279 (2½" bubble diameter).

A heavy duty plastic cooler liner bag 17 is then opened and placed inside of the cooler. The block/container units 10 and 12 are positioned inside of cooler 3 and liner bag 17 as illustrated. Preferably, liner bag 17 is clear so that the contents can be inspected without opening the bag. Also, it has been determined that a 3 mil. thickness is desirable to provide the necessary strength. A suitable liner bag (34"×34") is available from E. A. Bushmann Co. Another sheet of bubble-wrap 19 is used to fill the interstitial space surrounding block/container unit 10. Then, liner bag 17 is sealed off with a conventional, e.g., plastic, tie.

The primary objective with placement of the bubble-wrap is to use it where necessary to prevent shifting of the block/container units in coder 3 during shipping. In the embodiment of FIG. 1, it is unnecessary to place bubble-wrap between the sides of cooler 3 and block/container units 12, or between the two block/container units 12, since block/container units 12 are sized to fit snugly one beside the other crosswise in the cooler.

The top surfaces of block/container units 10 and 12 should remain exposed within liner bag 17. This facilitates ready removal of the sample containers from liner bag 17, and allows ice to be placed directly on top of the filled sample containers for the return trip to the lab. Additional layers of bubble-wrap 21 are placed on top of liner bag 17 as necessary to fill the remaining space.

Custody documents and seals, ID labels, field instructions, and like items for use by the customer, may be placed on top of bubble-wrap 21 in a sealed packet 23, e.g., a plastic Ziplock bag. Cover 3B is secured in place using a plurality of strap and clip assemblies, as will be described in connection with FIGS. 4-6.

The package sent to the customer may also include containers serving as a trip blank and temperature surrogate. In accordance with conventional practice, the trip blank is used as a control container to check for contamination occurring while the containers are en route from and returning to the lab. Similarly, the temperature surrogate provides a ready check of whether the sample containers have been maintained within the required temperature range.

On receipt, the customer opens the cooler, removes packet 23 and bubble-wrap 21, then opens liner bag 17, to gain ready access to the block/container units 10 and 12. After the block/container units have been removed, the containers are removed from the foamed plastic blocks, filled with sample material, then put back into the blocks. In this manner, foamed plastic blocks 9 and 11 provide convenient holders that maintain the containers upright and protect the sample containers outside as well as inside of the cooler.

The block/container units 10 and 12 are then returned to their original position inside of cooler 3 and liner bag 17. A layer of loose ice is poured on top of the block/container units and allowed to fall down the sides to maintain the temperature of the samples within the required range. To provide additional cooling, a layer of ice may also be provided in the bottom of liner bag 17 directly below block/container units 10 and 12. Bubble-wrap sheet 19 is used to fill remaining space around block/container unit 10. Liner bag 17 is tied off over the ice, and a layer of bubble-wrap 21 is repositioned on top before re-securing cover 3B to cooler body 3A.

By packaging the sample containers using foamed plastic blocks 9 and 11, and sheets of plastic bubble-wrap 15, 19 and 21, a tidy, efficient and secure package is obtained. Importantly, the packaging remains wholly in tact and functional even upon the addition of ice for the return of filled sample containers. Additionally, the bubble-wrap advantageously serves to increase the thermal insulation of the sample containers and ice. The risk of breakage is greatly reduced, and the sample containers remain readily accessible without the mess associated with conventional techniques involving the random dispersal of sample containers within loose packing material and/or ice. Liner bag 17 and absorbent pad 13 provide an added measure of safety against the leakage from the cooler of sample material or melted ice. The use of a clear liner bag allows inspection of the contents without opening the bag. As a result, contact with potentially hazardous sample materials can be avoided in the event of container breakage or leakage.

FIGS. 2 and 3 illustrate maximum volume configurations utilizing the same principles, and sharing the same advantages, as the first embodiment. To comply with DOT certification, and to afford adequate protection to the sample containers, the total weight of the 48 quart cooler should not exceed 56.4 lbs. (25.6 kg). The volume of sample material in the cooler should not exceed 75% of the total cooler volume.

Referring to FIG. 2, wherein elements also appearing in FIG. 1 are labelled with the same reference numerals, packaging arrangement 25 includes a cooler 3 having a cooler body 3A and cover 3B, an absorbent pad 13 covering the cooler bottom, and a plastic liner bag 17. In this embodiment, the arrangement of sample containers comprises a pair of block/container units 10 positioned on top of eight 1 quart Cubitainer containers 25

(Hedwin Co. No. CUB6050 or equivalent). Like container/block units 10 and 12, each Cubitainer 25 comprises a sealable glass container snugly retained within a foamed plastic block.

Three sheets of large size bubble-wrap 29A (2⅛″ bubble diameter) are used to line the interior of the cooler (preferably outside of liner bag 17). Two more sheets of large size bubble-wrap 29B are used to fill the interstitial space surrounding block/container units 10 (inside of liner bag 17). Two sheets of small size bubble-wrap 31A (13/16″ bubble diameter) are used to provide cushioning between block/container units 10 and Cubitainers 27. Two like sheets 31B are used to fill the remaining space between the top of closed off liner bag 17 and the inside of cover 3B.

In order to effectively cool the filled sample containers during the return trip, the customer should repack the containers as received, and add a layer of ice directly below and above each set of block/container units 10 and Cubitainers 27. If necessary to accommodate the ice, one or more sheets of bubble-wrap 31 may be omitted.

Referring now to FIG. 3, wherein elements also appearing in FIGS. 1 and/or 2 are labelled with the same reference numerals, a packaging arrangement 33 includes a cooler 3 having a cooler body 3A and cover 3B, an absorbent pad 13 covering the cooler bottom, and a plastic liner bag 17. In this embodiment, the arrangement of sample containers comprises a set of six one liter bottles 7 and corresponding foamed plastic blocks 11 forming six block/container units 12.

Three sheets of small size bubble-wrap 31C and one sheet of large size bubble-wrap 29C are placed between liner bag 17 and absorbent pad 13. Two sheets of small size bubble-wrap 31D are used to fill the interstitial spaces between adjacent pairs of block/container units 12, and two sheets of large size bubble-wrap 29D are placed between the inside endwalls of cooler body 3A and the block/container units 12 adjacent thereto. One layer of large size bubble-wrap 29E and two layers of small size bubble-wrap 31E are used to fill the remaining space between the top of closed-off liner bag 17 and the inside of cover 3B.

As in the previous embodiments, in order to effectively cool the filled sample containers during the return trip, the customer should repack the containers as received and add a layer of ice directly below and above each set of block/container units 12. If necessary to accommodate the ice, one or more sheets of bubble-wrap 31E, 29E may be omitted.

Referring to FIGS. 4 and 5, the arrangement for releasably securing cooler cover 3B on cooler body 3A is now described in detail. As previously mentioned, standard arrangements for securing a cover on a recreational-type cooler are inadequate to withstand the rigors of freight handling. In accordance with the present invention, external closure latches and/or hinges, if present, are removed, and a plurality of strap and clip assemblies 33 are installed to hold cover 3B tightly and securely over the opening of cooler body 3A. In the illustrated embodiment, a pair of strap and clip assemblies 33 are conveniently provided on opposing ends of cooler 3, on opposite sides of integrally molded cooler handles 36. Advantageously, handles 36 protrude outwardly and serve to protect assemblies 33 from sever impacts that might otherwise damage the clips during shipping.

Each assembly 33 comprises a pair of short relatively flexible straps, e.g., of nylon or the like. A first strap 34 is attached to the side of cooler cover 3B and has a first clip member 35 attached at the opposite end. A second strap 37 is attached to the side of cooler body 3A and has a second clip member 39 attached at the opposite end.

While various known fasteners can be used for securing the straps 34 and 37 to the cooler body and cover, it has been found that the use of two sheet metal screws affords greater strength over the use of rivets. Additionally, the fasteners should be made of a material that is resistant to corrosion in the presence of the hazardous materials to be transported. It is preferred that the straps be secured to the cooler body and cover using two zinc ½″ combo pan head sheet metal screws (e.g., No. 10 screw sold by Midwest Fastner, Inc. of Kalamazoo, Mich.) screwed through the straps and directly (without predrilling) into the outer walls of the high density polyethylene cooler shells.

First and second clip members 35, 39 form mating halves of a conventional plastic molded snap-clip (buckle) of the type disclosed in Tracy U.S. Pat. No. 4,150,464. That patent is hereby incorporated by reference. Such a buckle is sold as the Fastex #SR1 by ITW Nexus Co. of Wooddale, Ill.

Generally, first clip member 35 comprises a pair of resilient locking elements (arms), and second clip member 39 comprises a locking slot for receiving the arms of the first clip member in such a manner that the first clip member is snappingly engageable with the second clip member. The clip members remain securely locked together until finger pressure is applied to release the arms from the locking slot.

Advantageously, strap and clip assemblies 33 are inexpensive and readily applied to existing recreational-type coolers. Moreover, the strap and clip assemblies afford the strength and durability (including resistance to corrosion) required for the freight transportation hazardous sample materials. At the same time, the assemblies allow for quick and simple opening and closing of the cooler.

FIG. 6 illustrates a fourth embodiment of the invention utilizing a 10 quart capacity insulated cooler 41 having cooler body 41A and integrally hinged cover 41B. Such a cooler is manufactured and sold as the Coleman FlipLid10 (Coleman model No. 5210). In this embodiment, a single strap and clip assembly 33 is positioned on the front of the cooler, opposite the integrally hinged backside. Sample containers may be packed into cooler 4 1 utilizing the components and principles described in connection with the embodiments of FIGS. 1–3. In particular, cooler 41 is sufficiently large to allow a single block/container unit 10 or 12 to be packed therein, along with an absorbent pad, liner bag, and bubble-wrap filling the remaining cooler space.

The invention has been described in terms of presently preferred embodiments thereof. Other embodiments and variations within the scope and spirit of the invention as defined in the appended claims will, given the benefit of this disclosure, occur to those having ordinary skill in the art.

We claim:

1. A package for transporting temperature sensitive soil and water samples, comprising:
   a relatively rigid outer container having heat insulative walls defining an interior space; and a plurality of packing elements contained within and substantially filling said interior space, said packing elements including:
 a sealable sample container;
 a foamed, plastic block having an internal cavity, said sample container being snugly retained within said internal cavity; and
 plastic bubble-wrap at least partially surrounding said sample container and block, and substantially filling the interstitial interior space of the outer container.

2. A package according to claim 1, wherein said packing elements further comprise a plastic liner bag surrounding said foamed plastic block and sample container.

3. A package according to claim 1, wherein said packing elements further comprise a layer of liquid absorbent material covering a bottom surface of the container.

4. A package according to claim 2, wherein said packing elements further comprise a layer of liquid absorbent material covering a bottom surface of the container.

5. A package according to claim 1, wherein said packing elements include a plurality of sealable sample containers.

6. A package according to claim 1, wherein said packing elements include a plurality of foamed plastic blocks having an internal cavity.

7. A package according to claim 5, wherein said plurality of sample containers are snugly retained in respective recesses of a plurality of foamed plastic blocks.

8. A package according to claim 1, wherein said foamed plastic block comprises a plurality of recesses snugly retaining a plurality of respective sample containers.

9. A package according to claim 5, wherein said plurality of sample containers comprise sample containers of at least two different sizes.

10. A package for transporting temperature sensitive soil and water samples, comprising:
 a relatively rigid outer container, said container including:
  a container body having relatively rigid heat insulative wall panels forming container sides and a container bottom, said container body defining an interior space and a container opening;
  a relatively rigid heat insulative container cover fittable over said container opening to substantially seal the same, and being movable to open and close said container; and
  a strap and clip assembly for removably securing said container cover over said container opening, each said strap and clip assembly including:
   a first relatively flexible strap having a first clip member attached at one end thereof, and an opposite end attached to one of said container body and said container cover, said first clip member comprising a resilient locking element; and
   a second relatively flexible strap having a second clip member attached at one end thereof, and an opposite end attached to one of said container body and said container cover, said second clip member comprising a locking slot for receiving said resilient locking element in such a manner that the first clip member is snappingly engageable with said second clip member; and
 a plurality of packing elements contained within and substantially filling said interior space, said packing elements including:
  a sealable sample container;
  a foamed plastic block having an internal cavity, said sample container being snugly retained within said internal cavity; and
  plastic bubble-wrap at least partially surrounding said sample container and block, and substantially filling the interstitial interior space of the outer container.

* * * * *